US008889417B2

(12) United States Patent
Okano et al.

(10) Patent No.: US 8,889,417 B2
(45) Date of Patent: Nov. 18, 2014

(54) EPIDERMAL CULTURED CELL SHEET, MULTI-LAYERED CULTURED SKIN SHEET AND PROCESSES FOR PRODUCING THOSE SHEETS

(75) Inventors: Teruo Okano, Chiba (JP); Masayuki Yamato, Tokyo (JP); Mika Utsumi, Chiba (JP); Ai Kushida, Tokyo (JP); Chie Konno, Tokyo (JP); Akihiko Kikuchi, Tokyo (JP)

(73) Assignee: Cellseed Inc., Tokyo (JP)

( * ) Notice: Subject to any disclaimer, the term of this patent is extended or adjusted under 35 U.S.C. 154(b) by 1024 days.

(21) Appl. No.: 10/333,468

(22) PCT Filed: Jul. 2, 2001

(86) PCT No.: PCT/JP01/05723
§ 371 (c)(1),
(2), (4) Date: Jun. 16, 2003

(87) PCT Pub. No.: WO02/10349
PCT Pub. Date: Feb. 7, 2002

(65) Prior Publication Data
US 2004/0028657 A1 Feb. 12, 2004

(30) Foreign Application Priority Data
Jul. 21, 2000 (JP) .................................. 2000-221383

(51) Int. Cl.
*C12N 5/07* (2010.01)
*A61L 27/38* (2006.01)
*A61L 27/60* (2006.01)
*C12N 5/071* (2010.01)
*A61L 27/36* (2006.01)

(52) U.S. Cl.
CPC ....... *A61L 27/3804* (2013.01); *C12N 2502/094* (2013.01); *C12N 2502/1323* (2013.01); *A61L 27/60* (2013.01); *C12N 5/0698* (2013.01); *A61L 27/362* (2013.01); *C12N 2539/10* (2013.01)
USPC ........................... 435/402; 435/373; 424/93.7

(58) Field of Classification Search
CPC ........................... C12N 5/0629; C12N 5/0656
USPC .............. 435/325, 366, 395, 401, 402, 287.2; 427/2.11; 424/93.7
See application file for complete search history.

(56) References Cited

U.S. PATENT DOCUMENTS

| | | | |
|---|---|---|---|
| 4,016,036 A | 4/1977 | Green | |
| 4,485,097 A * | 11/1984 | Bell | 424/549 |
| 5,543,318 A | 8/1996 | Smith et al. | |
| 5,693,332 A * | 12/1997 | Hansbrough | 424/426 |
| 2002/0177221 A1 * | 11/2002 | Nishiguchi et al. | 435/287.2 |
| 2003/0219889 A1 * | 11/2003 | Sumaru et al. | 435/287.1 |
| 2004/0009566 A1 | 1/2004 | Okano et al. | |

FOREIGN PATENT DOCUMENTS

| | | |
|---|---|---|
| JP | 5-192138 A | 8/1993 |
| WO | 81/01416 A1 | 5/1981 |
| WO | WO 99/66036 | 12/1999 |

OTHER PUBLICATIONS

Yuuji Shirankata et al. , "Baiyou Hifu no Aratana Tenkai; Sanjigen Baiyou Hifu no Sakusei", Soshiki Baiyou Kougaku, Mar. 25, 1999, vol. 25, No. 3, pp. 109 to 111, especially, p. 110, right column, lines 27 to 30.
Masayuki Yamamoto et al., "Ondo Outou-sei Baiyo-sara Kara Hishinshuu-teki ni Kaishuu shita Saibou sheet no Seika-teki Kaiseki to Soshiki Kougaky e no Ouyou", Tokyo Joshi Ika Daigaku Sougou Kenkyusho Kiyou, !(1998), vol. 19, pp. 173 to 174, especially, p. 173, lines 23 to 26.
Akihiko Kikuchi et al., "Two-dimensional manipulation of confluently cultured vascular endothelial calls using temperature-responsive poly(N-isopropylarcrylamide)-grafted surface", Journal of Biomaterials Science Polymer Edition, (1998), vol. 9, No. 12, pp. 1331 to 1348, especially, Fig .1.
Yuuji Shirakata et al., "Baiyou Hifu no Rinshou Ouyou", Nippon Hifu-ka Gakkai Zasshi, Aug. 20, 1999, Vo. 109 No. 9, pp. 1301 to 1307.
Supplementary European Search Report dated Aug. 7, 2007, issued in connection with EP 01 94 5763.9.
Hirose et al, "Temperature-Responsive Surface for Novel Co-Culture Systems of Hepatocytes with Endothelial Cells: 2-D Patterned and Double Layered Co-Cultures", Yonsei Medical Journal, vol. 41, No. 6, pp. 803-813, 2000.
Hirose et al, "Creation of Designed Shape Cell Sheets That Are Noninvasively Harvested and Moved onto Another Surface", Biomacromolecules 2000, 1, pp. 377-381.
Kushida et al, "Two-dimensional manipulation of differentiated Madin-Darby canine kidney (MDCK) cell sheets: The noninvasive harvest from temperature-responsive culture dishes and transfer to other surfaces", Journal of Biomedical Materials Research, vol. 54, pp. 37-46, 2001.
Communication dated Sep. 21, 2009, issued in connection with corresponding European Patent Application No. 01 945 763.9.
http://www.answers.com/topic/upper-critical-solution-temperature and http://www.answers.com/topic/lower-critical-solution-temperature, Sep. 15, 2009, pp. 1-3.
English machine translation of JP 05-192138, published Aug. 3, 1993.

(Continued)

*Primary Examiner* — Allison Fox
(74) *Attorney, Agent, or Firm* — Nixon & Vanderhye P.C.

(57) ABSTRACT

A process for producing a cultured multi-layered skin cell sheet is provided.

13 Claims, 7 Drawing Sheets

(56) References Cited

OTHER PUBLICATIONS

Akins et al, Cardiac Organogenesis in Vitro: Reestablishment of Three-Dimensional Tissue Architecture by Dissociated Neonatal Rat Ventricular Cells, 1999, Tissue Engineering, vol. 5, p. 103-115.

Shimizu, Cardiac Tissue Engineering—Myocardial Tissue Construction using Biomaterials, 2000, Igaku no Ayumi, vol. 195, p. 203-204.

Soejima et al, "Effect of Cultured Endothelial Cells on Angiogenesis in Vivo" Plastic Reconstructive Surgery, 1998, vol. 101, p. 1552-1559.

Eppenberger et al, "In vitro reestablishment of cell-cell contacts in adult rat cardiomyocytes. Functional role of transmembrane components in the formation of new intercalated disk-like cell contacts", The FASEB Journal, 1999, vol. 13, p. S83-89.

Oyamada et al, "The Expression, Phosphorylation, and Localization of Connexin 43 and Gap-Junctional Intercellular Communication during the Establishment of a Synchronized Contraction of Cultured Neonatal Rate Cardiac Myocytes", Experimental Cell Research, vol. 212, p. 351-358 (1994).

Li et al, "In Vivo Survival and Function of Transplanted Rat Cardiomyocytes", Circulation Research, 1996; vol. 78, p. 283-288.

Goshima "Shirankata Baiyou-hou no Hatten, Genjou, Mirai, Junkan Seigyo" Dec. 30, 1993, vol. 14, No. 4, pp. 495-50.

Shimizu et al, "Two-dimensional manipulation of cardiac myocyte sheets utilizing temperature-responsive culture dishes augments the pulsatile amplitude", Tissue Engineering, Apr. 2001, vol. 7, No. 2, pp. 141-151.

Supplementary European Search Report dated Jul. 31, 2007, issued in connection with EP 01 94 5762.1.

Vande Berg et al, "Comparative growth dynamics and morphology between cultured myofibroblasts from granulating wounds and dermal fibroblasts", American Journal of Pathology, 1984, vol. 114, p. 187-200.

Zund et al, "Tissue engineering: A new approach in cardiovascular surgery; seeding of human fibroblasts followed by human endothelial cells on resorbable mesh", European Journal of Cardio-thoracic Surgery, 1998, vol. 13, p. 160-164.

Communication dated Sep. 10, 2009, issued in connection with corresponding European Patent Application No. 01 945 762.1.

http://www.answers.com/topic/lower-critical-solution-temperature (pp. 1-3), Sep. 3, 2009 and http://www.answers.com/topic/upper-critical-solution-temperature (pp. 1-2) Sep. 3, 2009.

* cited by examiner

E-cadherin

Laminin 5 (γ2)

EPIDERMAL CULTURED CELL SHEET, MULTI-LAYERED CULTURED SKIN SHEET AND PROCESSES FOR PRODUCING THOSE SHEETS

This is a 371 U.S. National Phase of Application PCT/JP01/05723, filed 2 Jul. 2001.

TECHNICAL FIELD

This invention relates to an epidermal cultured cell sheet, a multi-layered cultured skin sheet, processes for producing those sheets and a therapeutic method using those sheets.

BACKGROUND ART

When skin damage such as burn occurs, one should be most careful about bacterial infection from the skin injured by burn and the like. The dead skin is particularly susceptible to extensive proliferation of miscellaneous germs. Therefore, the dead skin must be removed to ensure that no miscellaneous germs will proliferate. However, removal of the skin provides a site for bacterial infection. In order to prevent such bacterial infection, the site from which the skin has been removed must be masked with a suitable material to avoid the ingress of bacteria. Masking materials that can be used for this purpose include synthetic polymer materials and a cultured skin. However, synthetic polymers can potentially cause rejection and the like and are not preferred as skin grafts. On the other hand, the cultured skin is a portion of the normal skin of the patient himself that has been cultured to a desired size, so it can be used without any possible inconvenience such as rejection and may well be described as the most natural masking material.

Cell culture of the kind described above has conventionally been performed on the glass surface or the surfaces of synthetic polymers subjected to various treatments. For example, a variety of vessels and the like that are made of polystyrene and which have been subjected to surface treatments such as irradiation with γ-rays and silicone coating are extensively used as cell culture vessels. Cells that have been cultured and grown in such cell culture vessels are peeled off and recovered from the surface of the vessel by treatment with proteolytic enzymes such as trypsin or chemicals.

However, several defects have been pointed out to exist in the recovery of grown cells by such treatment with chemicals; for one thing, the process of treatment is complicated enough to increase the possibility of contamination by impurities; second, the grown cells are denatured or damaged by the chemical treatment and their inherent functions are injured in some cases. With a view to overcoming these difficulties, several techniques have so far been proposed.

Japanese Patent Publication No. 23191-1990 describes a method of producing transplantable membranes of keratinous tissue by culturing keratinocytes from a human newborn in a culture vessel under conditions where a membrane of keratinous tissue is formed upon the surface of the vessel and enzymatically peeling off the membrane of keratinous tissue. Disclosed specifically is a technique in which 3T3 cells are grown as a feeder layer and piled up in multiple layers and the resulting cellular sheet is recovered with a proteolytic enzyme Dispase. However, the method described in the patent has had the following defects.

(1) Dispase is of bacterial origin and the recovered cellular sheet must be washed thoroughly.
(2) The conditions of treatment with Dispase differ from one cultured cell to another and the treatment requires great skill.
(3) The cultured epidermal cells are activated pathologically by Dispase treatment.
(4) Dispase treatment decomposes the extracellular matrix.
(5) As a result, the diseased part to which the recovered cellular sheet has been grafted is susceptible to infection.

Japanese Patent Laid-Open No. 192138/1993 describes a method of culturing skin cells by preparing a cell culture support having a substrate surface coated with a polymer whose upper or lower critical solution temperature in water is 0~80° C., culturing skin cells on the cell culture support at a temperature either below the upper critical solution temperature or above the lower critical solution temperature and thereafter peeling off the cultured skin cells by bringing the temperature to either above the upper critical solution temperature or below the lower critical solution temperature. In this method, temperature change is employed to peel off the cells from the culture substrate coated with the temperature-responsive polymer; however, the method does not permit efficient cell peeling and the obtained cellular sheet has had a lot of structural defects.

DISCLOSURE OF THE INVENTION

The present invention has been accomplished in an attempt at solving the aforementioned problems of the prior art. Thus, an object of the invention is to provide an epidermal cultured cell sheet or a multi-layered cultured skin sheet that has only a few structural defects as they are recovered with intracellular desmosome structures and the cell-to-substrate basal membrane protein being kept intact. Another object of the invention is to provide a method characterized by changing the environmental temperature without treatment with an enzyme such as Dispase and by using a polymer membrane so that cultured and grown cells can be peeled off and recovered from the surface of a support easily and without deforming their morphology.

In order to attain these objects, the present inventors performed research and development making a review from various angles. As a result, they found a technique in which when cells were cultured on a cell culture support having a substrate surface coated with a temperature-responsive polymer, with the cultured cell layer being optionally allowed to form multiple layers, and the temperature of the culture solution was thereafter brought to above an upper critical solution temperature or below a lower critical solution temperature so that the cultured epidermal cell sheet or multi-layered skin sheet would be in close contact with the polymer membrane, with the sheet being then peeled off together with the polymer membrane. The inventors found that the thus obtained epidermal sheet or multi-layered skin sheet had only a few structural defects. The present invention has been accomplished on the basis of this finding.

Thus, the present invention provides an epidermal cultured cell sheet or a multi-layered cultured skin sheet that has only a few structural defects as they are recovered with intracellular desmosome structures and the cell-to-substrate basal membrane protein being kept intact.

The present invention also provides a process for producing an epidermal cultured cell sheet or a multi-layered cultured skin sheet, which comprises culturing cells on a cell culture support having a substrate surface coated with a temperature-responsive polymer whose upper or lower critical solution temperature in water is 0~80° C., optionally forming multiple cultured cell layers by a conventional technique, and subsequently:
(1) bringing the temperature of the culture solution to above the upper critical solution temperature or below the lower critical solution temperature;
(2) bringing the cultured epidermal cell sheet or multi-layered skin sheet into close contact with the polymer membrane; and
(3) peeling the adhering sheet off together with the polymer membrane.

The invention further provides a process for producing a multi-layered cultured skin sheet, in which the epidermal cultured cell sheet or multi-layered cultured skin sheet in close contact with the polymer membrane as obtained by the above-described process is again allowed to adhere to a cell culture support, a cell culture support coated with a temperature-responsive polymer, a polymer membrane, other cellular sheet, etc. and the polymer membrane in close contact is thereafter peeled off to form multiple cultured cell layers.

In addition, the present invention provides the above-described epidermal cultured cell sheet or multi-layered cultured skin sheet which are adapted for use in the treatment of a burn and/or a wound that are gouged deep into a skin tissue.

Further in addition, the present invention provides a therapeutic method which comprises grafting the above-described epidermal cultured cell sheet or multi-layered skin culture sheet to a burn and/or a wound that are gouged deep into a skin tissue.

BEST MODE FOR CARRYING OUT THE INVENTION

Figure 1:
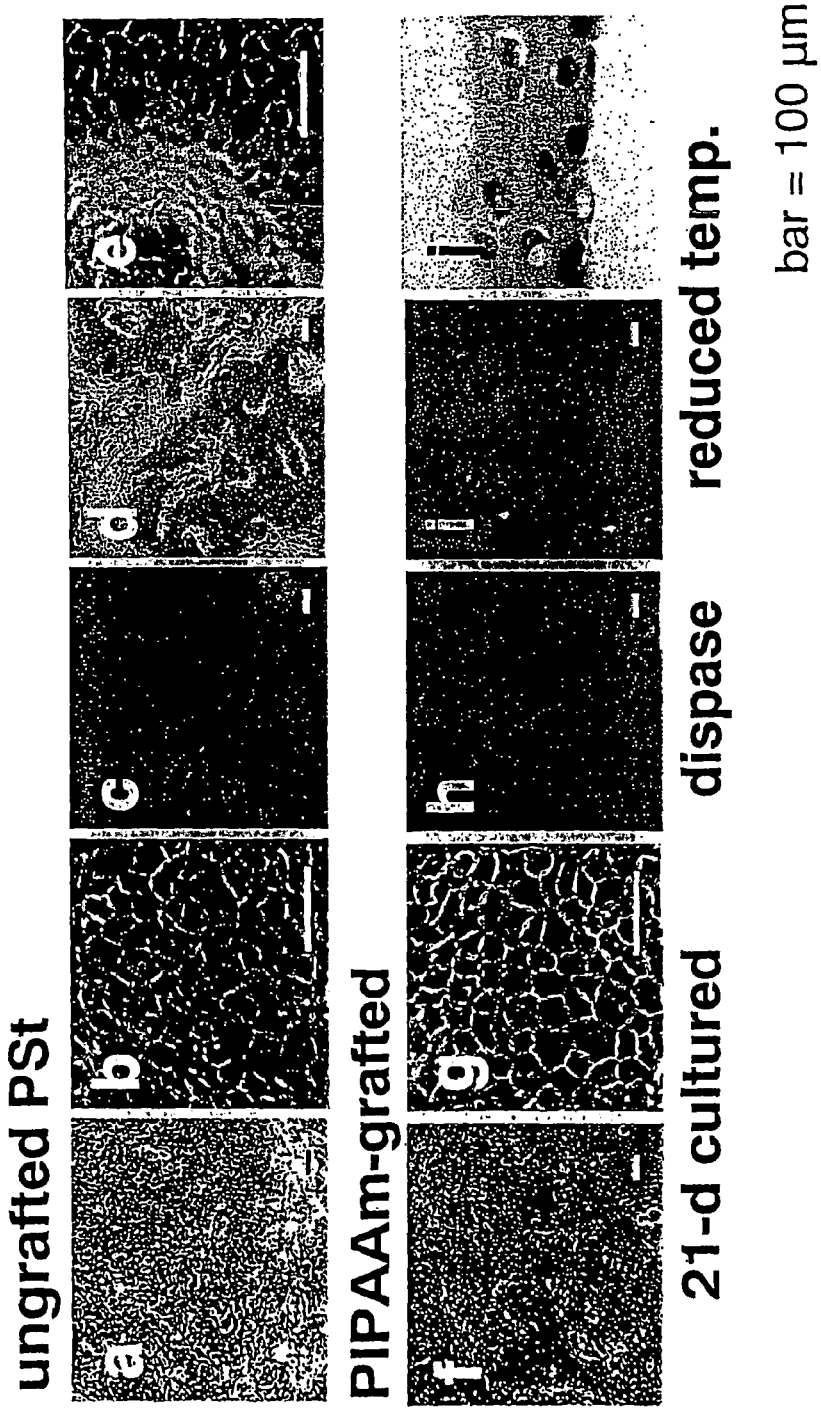
FIG. 1 is a set of micrographs showing how cultured skin sheets piled up under various conditions; the pictures in the upper row are micrographs of cells that were cultured on a usual culture dish to which no temperature-responsive polymer was grafted and the pictures in the lower row are micrographs of cells that were cultured on a culture dish to which polyisopropyl acrylamide (PIPAAm) was grafted.

Epidermal cells may be mentioned as cells that are preferred for use in preparing the epidermal cultured cell sheet or multi-layered cultured skin sheet of the invention. The epidermal cells are not limited to any particular kinds. For example, keratinocytes, melanocytes, pilomotor cells, as well as follicular cells and the like may be mentioned; if the obtained cellular sheet or skin sheet is to be used for medical purposes, human keratinocytes are desirable. In the present invention, the epidermal cultured cell sheet means a sheet which, as described above, is obtained by first culturing on a culture support a monolayer of various cells that form the epidermis of the living body and by then peeling off the monolayer from the support; the multi-layered cultured skin sheet means a sheet comprising a multiple of such epidermal cultured cell sheets, taken either individually or in combination.

The epidermal cultured cell sheet or multi-layered cultured skin sheet in the present invention is such that they were not damaged by proteolytic enzymes typified by Dispase and trypsin during culture. Hence, the epidermal cultured cell sheet or multi-layered cultured skin sheet as peeled off from the substrate keeps intercellular desmosome structures intact, having only a few structural defects and presenting high strength. An advantage of this feature is that when the obtained cellular sheet or skin sheet is employed medical purposes such as skin grafting, the diseased part is completely isolated from the outside by the sheets of the invention and rendered less susceptible to infection. The sheets of the invention are also characterized in that the cell-to-substrate protein resembling the basal lamina that was formed during culture has not been destroyed enzymatically. This helps assure effective adhesion of the sheet to the tissue of the diseased part upon grafting and efficient treatment can be implemented. Described specifically, if a customary proteolytic enzyme such as trypsin is used, intercellular desmosome structures and the cell-to-substrate protein resembling the basal lamina are seldom kept intact and, hence, the cells become separate individually as they are peeled off from the substrate. Among the applicable proteolytic enzymes, Dispase which destroys practically all of the cell-to-substrate protein resembling the basal lamina is known to be capable of allowing the cells to be peeled off from the substrate while keeping 10~60% of desmosome structures intact. However, the obtained cellular sheet has only weak strength. In contrast, both desmosome structures and basal membrane protein each remain by at least 80% in the cellular sheet of the invention and the above-described various advantages can be obtained.

As described above, the epidermal cultured cell sheet or multi-layered cultured skin sheet of the invention retains both intercellular desmosome structures and cell-to-substrate basal membrane protein and still exhibits high strength; such sheets have never been obtainable by the prior art.

The temperature-responsive polymer used to coat the substrate of the cell culture support has an upper or lower critical solution temperature in aqueous solution which is generally in the range of 0° C.~80° C., preferably 20° C.~50° C. If the upper or lower critical solution temperature exceeds 80° C., cells may potentially die and this is not preferable. If the upper or lower critical solution temperature is lower than 0° C., the cell growth rate will usually drop by an extreme degree or cells will die, which is not preferable, either.

The temperature-responsive polymer to be used in the invention may be a homopolymer or a copolymer. Exemplary polymers are described in Japanese Patent Laid-Open No. 211865/1990. Specifically, they are obtained by homo- or co-polymerization of the following monomers. Useful monomers include, for example, (meth)acrylamide compounds, N-(or N,N-di)alkyl-substituted (meth)acrylamide derivatives and vinyl ether derivatives; in the case of copolymers, any two or more of these monomers may be employed. Further, those monomers may be copolymerized with other monomers, or one polymer may be grafted to another or two polymers may be copolymerized or a mixture of polymer and copolymer may be employed. If desired, polymers may be crosslinked to an extent that will not impair their inherent properties.

The substrate which is to be provided with coatings may be of any types including those which are commonly used in cell culture, as exemplified by glass, modified glass and compounds such as polystyrene and poly(methyl methacrylate), as well as substances that can generally be given shape, for example, polymer compounds other than those listed above and ceramics.

The method of coating the support with the temperature-responsive polymer is not limited in any particular way and it may be in accordance with the disclosure in Japanese Patent Laid-Open No. 211865/1990. Specifically, such coating can be realized by subjecting the substrate and the above-mentioned monomer or polymer to either one of electron beam (EB) exposure, irradiation with γ-rays, irradiation with uv rays, plasma treatment, corona treatment and organic polymerization reaction, or other techniques such as physical adsorption as achieved by coating application and kneading may be adopted.

In the present invention, cell culturing is performed on the cell culture support (e.g. cell culture dish) that has been prepared as described above. The temperature of the medium is not limited to any particular value; if the aforementioned polymer forming the coat on the substrate surface has an upper critical solution temperature, the temperature of the medium may be lower than such upper critical solution temperature; if said polymer has a lower critical solution temperature, the temperature of the medium may be higher than such lower critical solution temperature. Of course, culturing is inappropriate if it is in a low-temperature range where cultured cells do not grow or in a high-temperature range where cultured cells die. Culture conditions other than temperature may be as adopted in the conventional techniques and are not limited in any particular way. For example, the medium to be used may be one that is supplemented with sera such as known fetal calf serum (FCS); alternatively, it may be a serum-free medium or one which is not supplemented with any sera.

In the method of the invention, the culture time may be set in accordance with the aforementioned procedure to a value that suits the specific object of using the epidermal cultured cell sheet or multi-layered cultured skin sheet. In order to peel off and recover the cultured cells from the support material, the cultured epidermal cell sheet or multi-layered skin sheet is brought into close contact with the polymer membrane and the temperature of the support material in close contact with the cells is brought to above the upper critical solution temperature of the polymer with which the support's substrate is coated or below its lower critical solution temperature, whereby either sheet can be peeled off from the substrate together with the polymer membrane. Peeling of the sheets can be performed not only in the culture solution used to culture the cells but also in other isotonic solutions; a suitable solution can be chosen in accordance with a specific object. Examples of the polymer membrane that can be used to achieve close contact with the epidermal cell sheet or the multi-layered skin sheet include polyvinylidene difluoride (PVDF), polypropylene, polyethylene, cellulose and its derivatives, as well as chitin, chitosan, collagen, polyurethane, etc.

The method of producing the multi-layered cultured skin sheet according to the second aspect of the invention is not limited to any particular types; examples include a method in which generally known 3T3 cells are grown as a feeder layer and piled up in multiple layers, and a method of using the epidermal cultured cell sheet in close contact with the above-mentioned polymer membrane. The following methods may be given as specific examples.

(1) The cellular sheet in intimate contact with the polymer membrane is allowed to adhere to the cell culture support and thereafter a medium is added to peel off the polymer membrane from the cellular sheet; then, a cellular sheet in intimate contact with another polymer membrane is allowed to adhere to the first cellular sheet; this process is repeated to form a multiple of cellular sheets.

(2) The cellular sheet in intimate contact with the polymer membrane is turned over and fixed on the cell culture support such that the polymer membrane contacts the support; another cellular sheet is allowed to adhere to the first cellular sheet; thereafter, a medium is added to peel off the polymer membrane from the second cellular sheet, to which yet another cellular sheet is allowed to adhere; this process is repeated to form a multiple of cellular sheets.

(3) Two cellular sheets each in intimate contact with the polymer membrane are themselves brought into intimate contact with each other.

(4) The cellular sheet in intimate contact with the polymer membrane is applied to the diseased part of the living body and allowed to adhere to a living tissue; then, the polymer membrane is peeled off and another cellular sheet is superposed on the first cellular sheet.

The multi-layered cultured skin sheet of the invention is not necessarily composed of keratinocytes alone. For example, a cellular sheet or multi-layered skin sheet that are made of keratinocytes may be overlaid with a fibroblast sheet and/or angioendothelial cell sheet that have been prepared by similar operations. This technique is extremely effective in realizing a product even nearer to an in vivo skin tissue.

In order to peel off and recover the epidermal cultured cell sheet and multi-layered cultured skin cell in high efficiency, tapping on the cell culture support or shaking it gently, agitating the medium with a pipette and other methods may be employed either alone or in combination. In addition, the cultured cells may optionally be washed with an isotonic solution and the like to be peeled off and recovered.

The epidermal cultured cell sheet or multi-layered cultured skin sheet that are obtained by the method described above are very much superior to those obtained by the prior art methods in terms of both ease of peeling and non-invasiveness and hold great promise in clinical applications such as skin grafting. In particular, the multi-layered cultured skin sheet of the invention is distinct from the conventional cultured skin sheets in that it keeps the basal membrane protein intact; hence, when it is used as a skin graft, it will adhere viably to the tissue of the diseased part even if it is gouged deep. This means an improvement in the efficiency of treatment of the diseased part and even a smaller stress on the patient; the sheets of the invention will therefore prove to be a very effective technology. Further, the cell culturing method of the invention is an effective technology not only for keratinocytes but also for kidney cells, lung cells, mucous membrane or epithelial cells in various organs of the alimentary system. Note that the cell culture support to be used in the method of the invention can be used over and again.

EXAMPLES

On the pages that follow, the present invention is described in greater detail with reference to examples, which are by no means intended to limit the invention.

Example 1

Detachment and Recovery of Human Keratinocyte Sheets Cultured and Piled Up on Temperature-Responsive Culture Dish Materials
The following materials were used.
Cells: Human newborn keratinocytes (Sanko Junyaku Co., Ltd. CC-2503), NIH3T3 cells
Culture dish: Temperature-responsive culture dish H003 (1.9 μg/cm$^2$), Falcon 3001 as a control
Medium: DMEM+AB (to prepare a feeder layer), medium of Greene et al. (for human newborn keratinocytes)
Mitomycin C (Wako Pure Chemical Industries, Ltd.)
Dispase (GODO SHUSEI CO., LTD.)
Durapore Membrane (hydrophilized PVDF membrane, Model No. SULP04700, product of MILLIPORE)
Method
NIH3T3 cells were plated onto a 35-mm$^\Phi$ culture dish (3001, H003) at a density of $2 \times 10^4$ cells/cm$^2$; after the cells adhered and expanded, the medium was replaced by a serum-free medium containing 16 μg/mL of mitomycin C; following a 2-hr treatment, human newborn keratinocytes were plated at a density of $5 \times 10^4$ cells/dish.

Three weeks later, the cells on H003 were detached by either treatment with 30 units/cm$^2$ of Dispase (GODO SHUSEI CO., LTD.) or low-temperature treatment in accordance with the following procedure. The cells on Falcon 3001 were detached by treatment with 30 units/cm$^2$ of Dispase (GODO SHUSEI CO., LTD.)
[Dispase Treatment]
After aspirating the medium, Durapore Membrane cut to the size of the 35-mm$^\Phi$ culture dish was placed on the cell layer and Dispase was added in 1-mL portions. After standing at room temperature for 30 minutes, the medium was aspirated and the cellular sheet was detached together with the membrane.
[Low-Temperature Treatment]
After aspirating the medium, Durapore Membrane cut to the size of the 35-mm$^\Phi$ culture dish was placed on the cell layer and incubation was performed at 20° C. for 30 minutes. Thereafter, the cellular sheet was detached by means of forceps such that it would rest on the membrane.
[Tissue Sections]
The membrane carrying the detached cells was transferred to a culture dish and fixed with 4% paraformaldehyde. For dehydration, the following procedure was repeated three times: i) standing in 70%, 80% and 90% ethanol, each for 10 minutes; ii) standing in 100% for about 1 hour; iii) standing in chloroform for 30 minutes in order to replace the alcohol by chloroform. Paraffin that had been melted at 61° C. was cast into the culture dish and incubated at 61° C. until it completely surrounded the sample; then, the paraffin was allowed to solidify at room temperature. The solidified paraffin was sliced into thin sections, which were stained with HE and examined under microscope.
Results
The results are shown in FIGS. 1~7.

FIG. 1 is a set of micrographs showing how cultured cell sheets piled up under various conditions. In FIG. 1, "ungrafted PSt" refers to the case of cultivation on a cell culture polystyrene dish uncoated with the temperature-responsive polymer; "PIPAAm-grafted" refers to the case of cultivation on a culture dish to which polyisopropyl acrylamide (PIPAAm) was grafted; "21-d cultured" means cultivation for 21 days; "dispase" means treatment with Dispase; "reduced temp." means low-temperature treatment; "bar=100 μm" means that the bar (either clear or solid) in each of FIGS. 1a~1j has a length of 100 μm.

Pictures a~e in the upper row are micrographs of cells that were cultured on an ordinary dish to which no temperature-responsive polymer was grafted. The magnification of each picture is indicated by the length of the bar; pictures a and b show the growth of cells cultured for 21 days, provided that picture a is a micrograph taken at low magnification and picture b at high magnification; picture c shows cultured cells that were treated with Dispase after 21 days of culture; pictures d and e show cells incubated at 20° C. for 30 minutes after 21 days of culture, provided that picture d was taken at low magnification and picture e at high magnification. Pictures f~j in the lower row are micrographs of cells that were cultivated on a culture dish to which polyisopropyl acrylamide (PIPAAm) was grafted; pictures f and g show the growth of cells cultured for 21 days, provided that picture f is a micrograph taken at low magnification and picture g at high magnification; picture h shows cultured cells that were treated with Dispase after 21 days of culture; pictures i and j show cells incubated at 20° C. for 30 minutes after 21 days of culture, provided that picture i was taken at low magnification and picture j at high magnification.

The results shown in FIG. 1 revealed the following: the culture dish to which polyisopropyl acrylamide was grafted (see the pictures in the lower row) enables as efficient cell cultivation as on the ordinary culture dish (see the pictures in the upper row) and, what is more, the grown cells can be peeled off in the form of a sheet by just lowering the temperature. No cellular sheet can be recovered from the ordinary culture dish.

Figure 2:
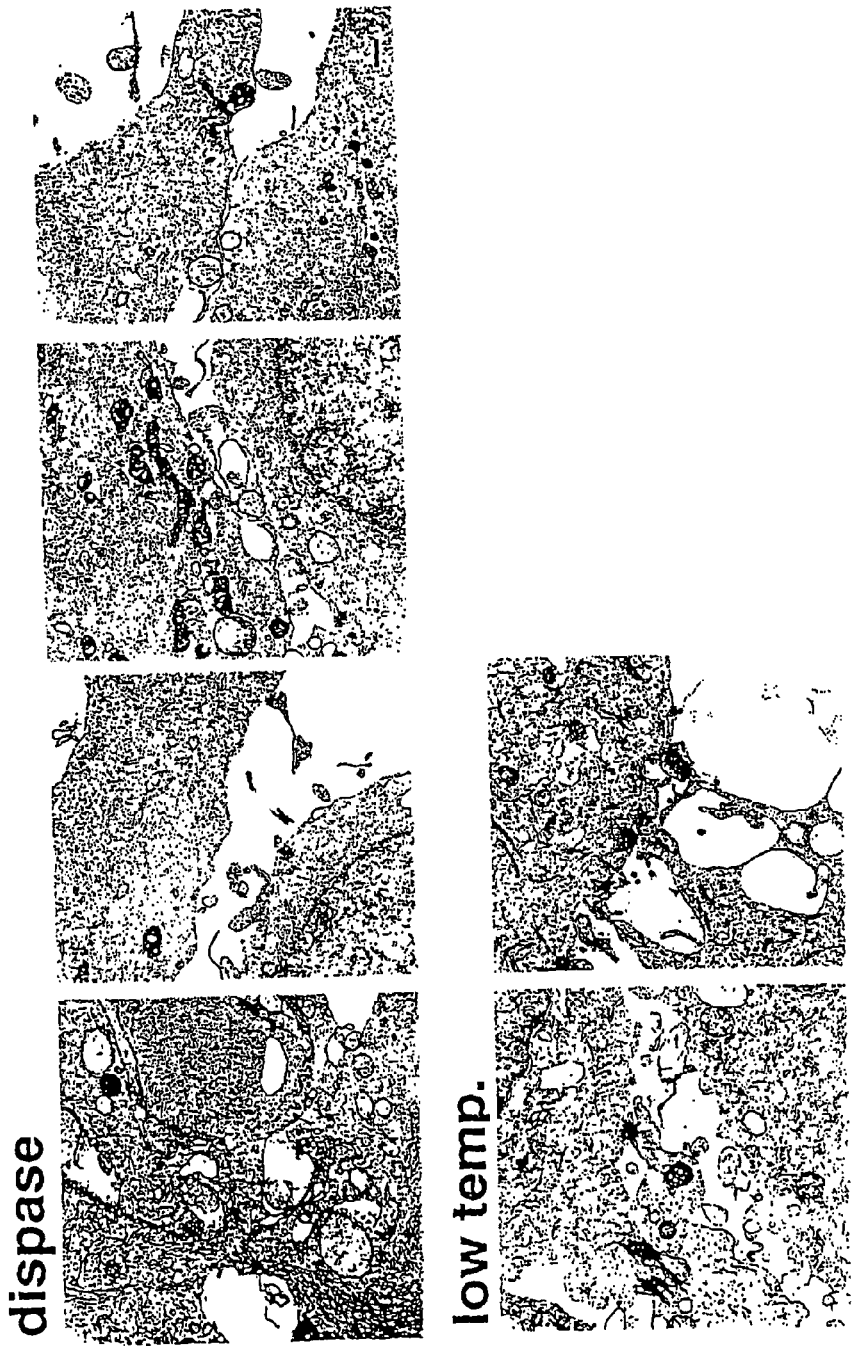
FIG. 2 is a set of micrographs of cells that were cultured on a culture dish to which polyisopropyl acrylamide (PIPAAm) was grafted; the upper row shows micrographs of cultured cells that were stained with HE after treatment with Dispase at 21 days of culture.

FIG. 2 is a set of micrographs of cells that were cultured on a culture dish to which polyisopropyl acrylamide (PIPAAm) was grafted. In FIG. 2, "dispase" means treatment with Dispase, and "low temp." means low-temperature treatment.

The pictures in the upper row of FIG. 2 are micrographs showing the result of HE staining of cells that were treated with Dispase after 21 days of culture. The pictures in the lower row are micrographs showing the result of HE staining of cells that were incubated at 20° C. for 30 minutes after 21 days of culture. The stained portions appear solid in the pictures; "dispase" means treatment with Dispase and "reduced temp." means low-temperature treatment.

The results shown in FIG. 2 revealed the following: in the cellular sheets obtained by low-temperature treatment (see the pictures in the lower row), the intercellular protein was stained (as indicated by the solid portions); in the cellular sheets obtained by treatment with Dispase (see the pictures in the upper row), there were no stained intercellular portions (no solid portions), indicating that the intercellular protein had disappeared from the cultured skin sheets.

Figure 3:
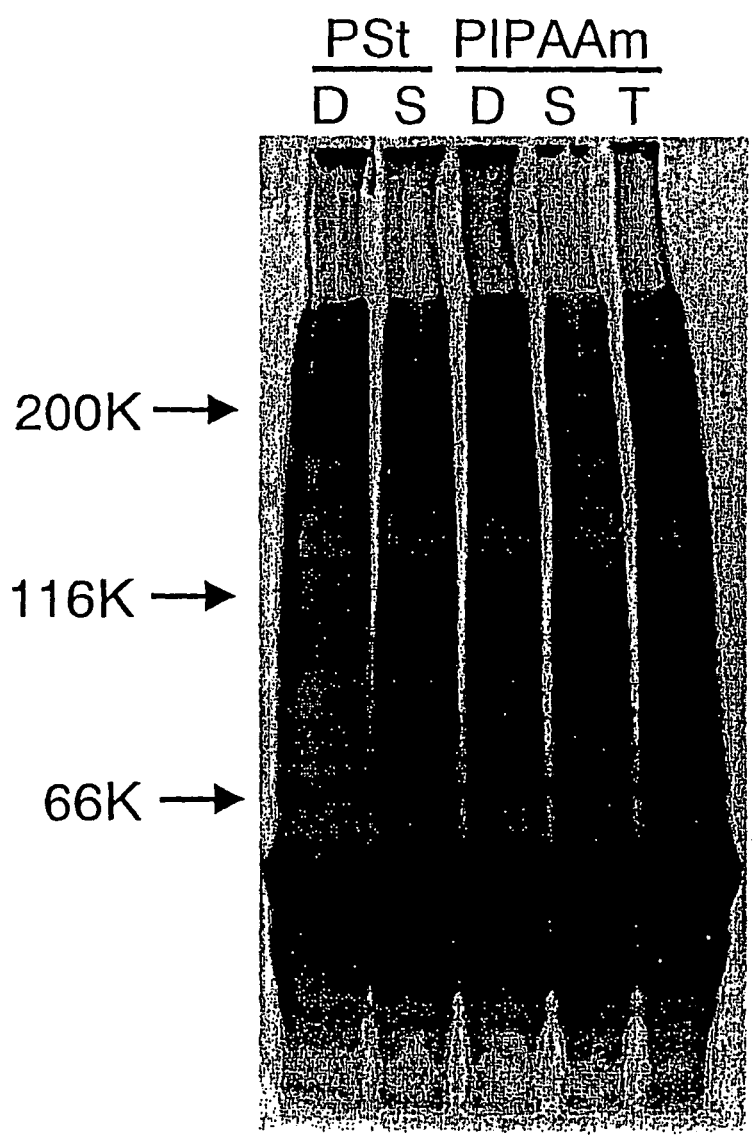
FIG. 3 is an electrophoretic picture showing the results of recovering the multi-layered cultured skin sheet on a temperature-responsive culture dish by either low-temperature treatment (incubating at 20° C. for 30 minutes) or Dispase treatment or physical stimulation (scraping with a spatula) and quantifying the total protein content of the cells by electrophoresis.

FIG. 3 is an electrophoretic picture showing the results of recovering the piled-up epidermal cell layers of Example 1 on a temperature-responsive culture dish by either low-temperature treatment (incubating at 20° C. for 30 minutes) or Dispase treatment or physical stimulation (scraping with a spatula) and quantifying the total protein content of the cells by electrophoresis. In FIG. 3, 66K refers to serum albumin, 116K refers to β-galactosidase, 200K refers to myosin, PSt refers to a cell culture polystyrene dish uncoated with a temperature-responsive polymer, PIPAAm refers to a polystyrene dish coated with polyisopropyl acrylamide, D refers to a cell layer recovered by Dispase treatment, S refers to a cell layer recovered by physical stimulation, and T refers to a cell layer recovered by low-temperature treatment. The results show that the kinds of protein that were present in the cells and their amounts did not change between the two types of culture dish or among the three methods of peeling off the cellular sheet.

Figure 4:
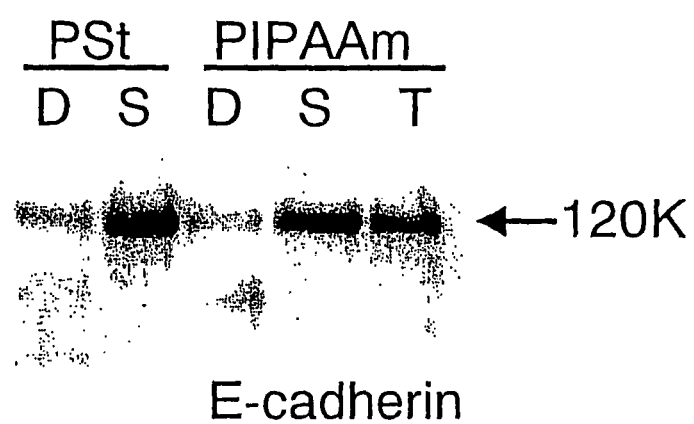
FIG. 4 is an electrophoretic picture showing the results of recovering the multiple epidermal cell layers on a temperature-responsive culture dish by either low-temperature treatment (incubating at 20° C. for 30 minutes) or Dispase treatment or physical stimulation (scraping with a spatula) and analyzing the recovered cell layers by western blotting with an anti-E-cadherin antibody or an anti-laminin 5 antibody.
Figure 4:
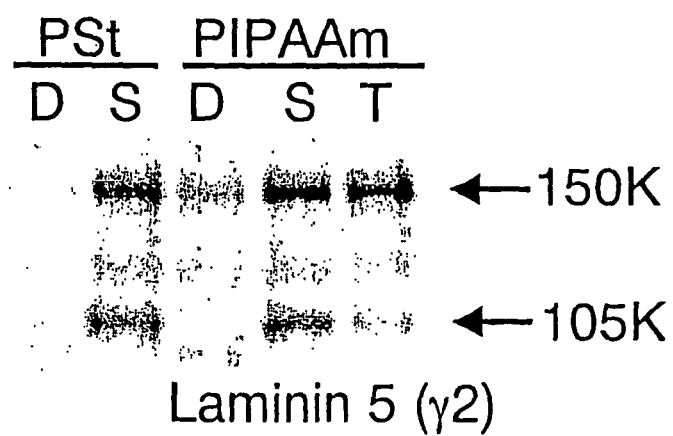

FIG. 4 is an electrophoretic picture showing the results of recovering the piled-up epidermal cell layers of Example 1 on a temperature-responsive culture dish by either low-temperature treatment (incubating at 20° C. for 30 minutes) or Dispase treatment or physical stimulation (scraping with a spatula) and analyzing the recovered cell layers by western blotting with an anti-E-cadherin antibody or an anti-laminin 5 antibody (indicated as Laminin 5(γ2). In FIG. 4, PSt, PIPAAm, D, S and T have the same meanings as defined for FIG. 3. The panel labelled E-cadherin shows the result of using an anti-E-cadherin antibody and the panel labelled Laminin 5(γ2) shows the result of using an anti-laminin 5 antibody. In FIG. 4, 120K refers to E-cadherin which is known to exist between cells, and 150K and 105K refer to laminin 5 (Laminin 5(γ2)) which is known to exist between a cell and the substrate. The results revealed the following.

(1) Ordinary Culture Dish (Made of Polystyrene)

In D (Dispase treatment), protein loss occurred. In S (scraping with a spatula), the protein was kept intact but the cells, being forcibly peeled off from the substrate, gave a cellular sheet having a lot of structural defects.

(2) Culture Dish to Which Polyisopropyl Acrylamide was Grafted

In D (Dispase treatment), protein loss occurred. In S (scraping with a spatula), the protein was kept intact but the cells, being forcibly peeled off from the substrate, gave a cellular sheet having a lot of structural defects. In T (low-temperature treatment, the inventive method), a cellular sheet was obtained that not only kept the protein intact but also had very few structural defects.

Figure 5:
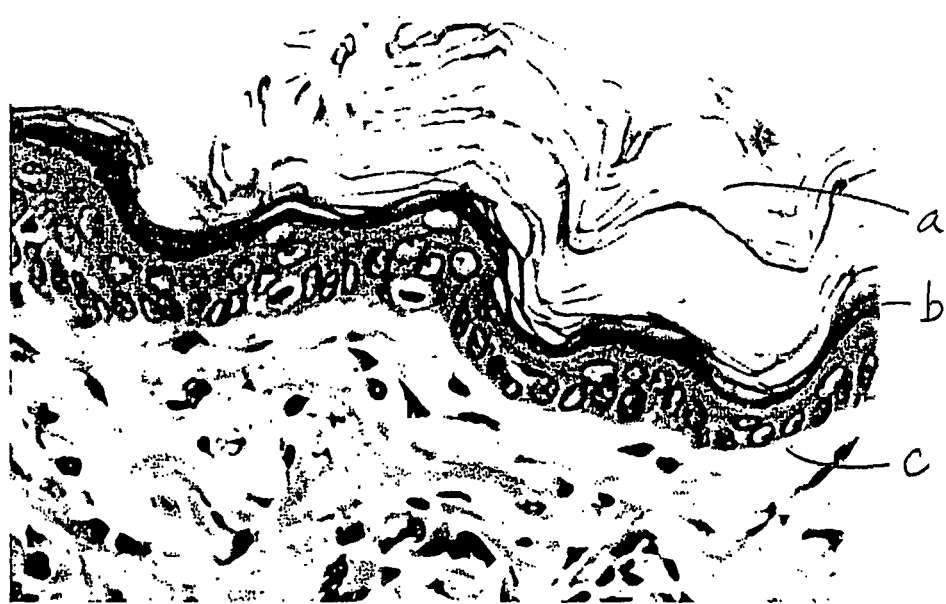
FIG. 5 is a micrograph of a tissue section showing the result of grafting to a nude rat the multi-layered cultured skin sheet of the invention as obtained by low-temperature treatment.

FIG. 5 is a micrograph showing the result of grafting to a nude rat (F344nu/nu (thymus-free rat), male, 4-week old) the multi-layered cultured skin sheet of the invention as obtained by low-temperature treatment in Example 1. In FIG. 5, the multi-layered cultured skin sheet is indicated by b and the rat's tissue by c; as indicated by a, the grafted skin sheet adhered viably to form a keratinized layer.

It is clear from FIG. 5 that the grafted multiple layers of cultured skin sheet of the invention viably adhered to the rat's tissue in a satisfactory manner (the boundary between b and c did not swell, nor did the grafted skin sheet peel off from the rat's tissue).

Figure 6:
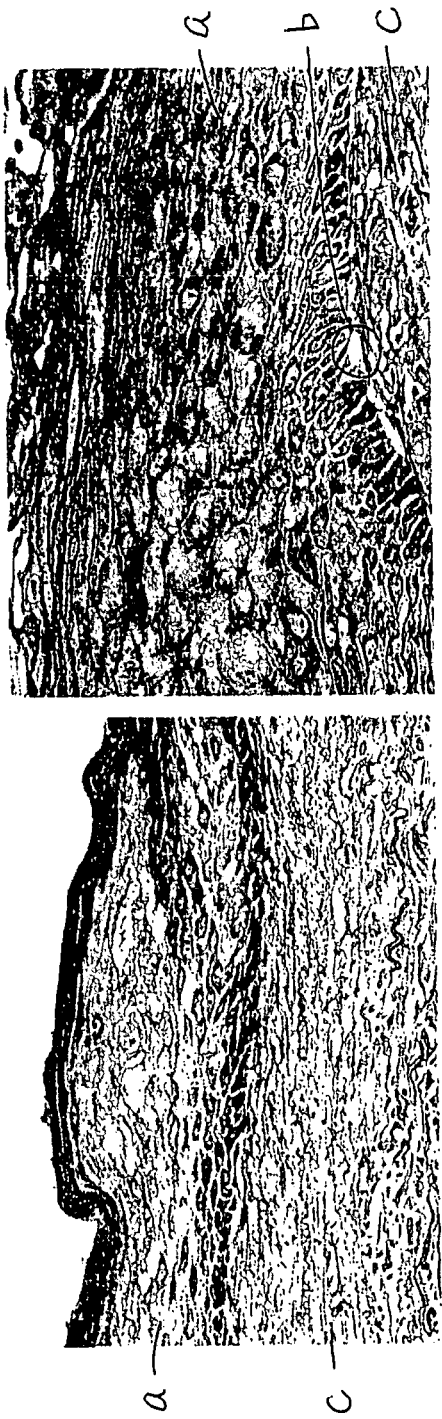
FIG. 6 is a set of micrographs showing the result of azan staining of tissue sections obtained by grafting to nude rats a multi-layered cultured skin sheet prepared by low-temperature treatment and a multi-layered cultured skin sheet prepared by Dispase treatment.
Figure 6:
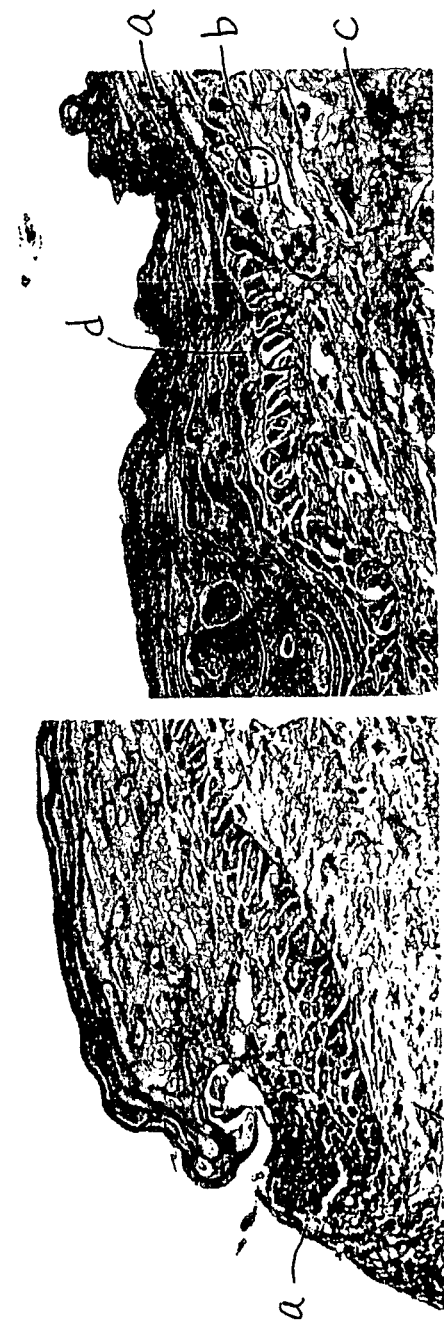
Figure 7:
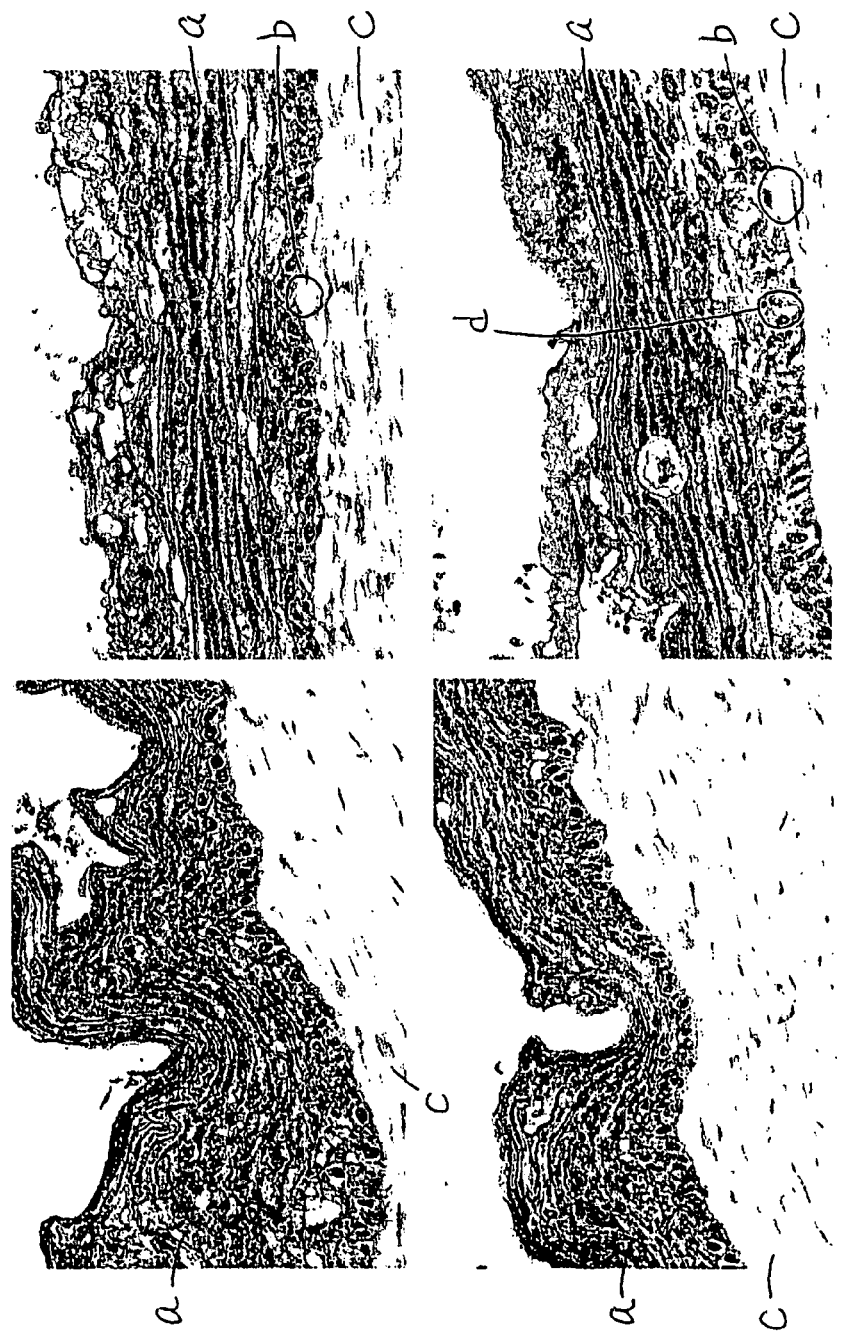
FIG. 7 is a set of micrographs showing the result of argentation of tissue sections obtained by grafting to nude rats a multi-layered cultured skin sheet prepared by low-temperature treatment and a multi-layered cultured skin sheet prepared by Dispase treatment.

FIGS. 6 and 7 show the results of azan staining and argentation, respectively, of the tissue sections shown in FIG. 5. In FIGS. 6 and 7, the grafted multiple layers of cultured skin sheet are indicated by a and the rat's tissue by c. The multiple layers of cultured skin sheet as obtained by low-temperature treatment viably adhered to the rat's tissue in a satisfactory manner. On the other hand, in the multiple layers of cultured skin sheet as obtained by treatment with Dispase, the basal lamina layer between a and c was interrupted by Dispase (as indicated by d) and empty cavities were formed between a and c (as indicated by b). It was therefore clear that the grafted skin sheet had the basal lamina interrupted and, hence, could not viably adhere to the living tissue in a satisfactory manner.

Example 2

Human fibroblasts ($2 \times 10^4$ cells/cm$^2$; KURABO INDUSTRIES, LTD.) were plated onto a 35-mm$^\Phi$ culture dish to which polyisopropyl amide (PIPAAm) had been grafted in an amount of 1.9 μg/cm$^2$ and the cells were cultured in the usual manner (on 20% bovine serum containing DMEM). Five days later, after confirming the confluency of the human fibroblasts, the medium was aspirated. Immediately thereafter, the multiple layers of cultured skin sheet in intimate contact with the polymer membrane as obtained in Example 1 from the PIPPAm-grafted culture dish by low-temperature treatment was placed over the human fibroblast sheet; thereafter, a medium of the same type as used in Example 1 was poured in gently and the polymer membrane was peeled off. By subsequent 2-day culture, the fibroblast sheet adhered to the multiple layers of cultured skin sheet. The multi-layered cultured skin sheet now carrying the fibroblast sheet was peeled off from the surface of the support by performing the same low-temperature treatment as in Example 1. The multi-layered cultured skin sheet was grafted to a nude rat as in Example 1 and compared with the multi-layered cultured skin sheet of Example 1. The results are shown in Table 1.

TABLE 1

| Skin sheet | Graftability | | |
| --- | --- | --- | --- |
| | Sheet strength | Adhering speed | Viability |
| Skin sheet of Example 1 | ○ | ○ | ○ |
| Skin sheet of Example 2 | ○ | ⊙ | ○ |

(Note)
⊙, excellent;
○, good

The foregoing results show that the multi-layered cultured skin sheet obtained in Example 2 also adhered viably to the rat's tissue in a satisfactory manner. In addition, this sheet had the advantage of reducing the time required to achieve viable adhering.

In Examples 1 and 2, "low-temperature treatment" was performed by incubation at 20° C. for 30 minutes but these temperature and time conditions are not the sole conditions for the "low-temperature treatment" to be conducted in the invention. The preferred temperature condition for the "low-temperature treatment" is 0~30° C. and the preferred time condition ranges from 2 minutes to 1 hour.

Example 3

A patient with a burn on the face was treated but a scar remained. With the patient's consent, the multi-layered cultured skin sheet of the invention was applied to treat the scar. Specifically, an epidermal cell membrane of the size 1 cm×1 cm was sampled from the patient's arm and disaggregated into individual cells by trypsinization in the usual manner. The cells were then cultivated in accordance with Example 1 both on a culture dish (H003) coated with polyisopropyl acrylamide and on an ordinary culture dish (control, Falcon 3001). Three weeks later, the multi-layered cultured skin sheet on the H003 substrate was peeled off by low-temperature treatment whereas the skin sheet on the control substrate was peeled off by treatment with Dispase.

The scar on the patient's face was generally gouged to the usual depth but gouged to a greater depth in selected areas. Thus, the wound was gouged in two different depths, to which each of the skin sheets were grafted. After one-week standing, the viability of the sheets that adhered to the wound was observed. The result is shown in Table 2.

TABLE 2

|  | Wound depth | |
| --- | --- | --- |
|  | shallow | deep |
| viability of the skin sheet obtained by low-temperature treatment | ◉ | ○ |
| Viability of the skin sheet Obtained by Dispase treatment | ○ | X |

(Note)
◉, excellent;
○, good;
X, poor

From the foregoing results, it can be seen that the skin sheet of the invention could viably adhere in a satisfactory manner to a wound that was gouged to a great depth that would have prevented the viable adhesion of the multi-layered cultured skin sheet that was recovered by treatment with Dispase. This achieves two major advantages: for one thing, the treatment is efficient and reduces the stress on the patient; secondly, the scar is gouged deep enough to ensure that the grafted skin sheet provides better aesthetic appeal. Hence, the multi-layered cultured skin sheet of the invention will constitute a very effective technology.

Industrial Applicability

The epidermal cultured cell sheet and multi-layered cultured skin sheet of the invention do not degrade E-cadherin or laminin 5 as contrasted with Dispase treatment and they still involve very few structural defects; these sheets hence hold great promise in clinical applications such as skin grafting. Therefore, the present invention is extremely useful in medical and biological fields, particularly in cell engineering and medical engineering.

The invention claimed is:

1. A process for producing a cultured multi-layered cell sheet adhered to a polymer membrane, wherein the cultured multi-layered cell sheet is used for grafting and has intracellular desmosome structures and intact cell-to-substrate basal membrane protein and said cell sheet consists of mucous membrane cells, said process comprising
    (1) culturing cells in culture solution on a temperature-responsive polymer which has been coated on a substrate surface of a cell culture support, wherein the temperature-responsive polymer has a lower critical solution temperature in water of 0-80° C., to form said cultured multi-layered cell sheet,
    wherein the temperature-responsive polymer is poly(N-isopropylacrylamide), and
    wherein the culture solution is a medium for multi-layer culture;
    (2) adjusting the temperature of the culture solution to below the lower critical solution temperature, whereby the substrate surface is made hydrophilic and adhesion of the cell sheet to the substrate is weakened;
    (3) adhering the cultured multi-layered cell sheet to the polymer membrane; and
    (4) peeling the cultured multi-layered cell sheet adhered to the polymer membrane from the substrate surface to obtain the cultured multi-layered cell sheet adhered to the polymer membrane.

2. A cultured multi-layered cell sheet adhered to a polymer membrane for grafting, wherein the cell sheet is produced by the process according to claim 1.

3. A therapeutic method in which the cultured multi-layered cell sheet produced by the process according to claim 1 is grafted to a burn and/or a wound that are gouged deep into a skin tissue.

4. A process for producing a cultured multi-layered cell sheet adhered to a polymer membrane, wherein said cell sheet is used for grafting and consists of fibroblasts or angioendothelial cells and mucous membrane cells, comprising
    (1) providing a cellular sheet or multi-layered cell sheet adhered to a temperature-responsive polymer which has been coated on a cell culture support, wherein the temperature-responsive polymer has a lower critical solution temperature in water of 0-80° C. and is poly(N-isopropylacrylamide), wherein the cellular sheet is provided in culture solution, and wherein the cellular sheet consists of fibroblasts or angioendothelial cells;
    (2) adhering the cultured multi-layered cell sheet adhered to the polymer membrane obtained by the process according to claim 1 to the cellular sheet or multi-layered cell sheet provided in step (1);
    (3) adjusting the temperature of the culture solution to below the lower critical solution temperature, whereby the substrate surface is made hydrophilic and adhesion of the cell sheet to the substrate is weakened; and
    (4) peeling the cultured multi-layered cell sheet adhered to the polymer membrane from the substrate surface without treatment with a proteolytic enzyme to obtain the cultured multi-layered cell sheet adhered to the polymer membrane.

5. A cultured multi-layered cell sheet adhered to a polymer membrane for grafting, wherein the cell sheet is produced by the process according to claim 4.

6. A therapeutic method in which the cultured multi-layered cell sheet produced by the process according to claim 4 is grafted to a burn and/or a wound that are gouged deep into a skin tissue.

7. A process for producing a cultured multi-layered cell sheet adhered to a polymer membrane, wherein the cultured multi-layered cell sheet is used for grafting and has intracellular desmosome structures and intact cell-to-substrate basal membrane protein and said cell sheet comprises mucous membrane cells, said process comprising
    (1) culturing cells in culture solution on a temperature-responsive polymer which has been coated on a substrate surface of a cell culture support, wherein the temperature-responsive polymer has a lower critical solution temperature in water of 0-80° C., to form said cultured multi-layered cell sheet
    wherein the temperature-responsive polymer is poly(N-isopropylacrylamide), and
    wherein the culture solution is a medium for multi-layer culture;
    (2) adjusting the temperature of the culture solution to below the lower critical solution temperature, whereby the substrate surface is made hydrophilic and adhesion of the cell sheet to the substrate is weakened;
    (3) adhering the cultured multi-layered cell sheet to the polymer membrane; and (4) peeling the cultured multi-layered cell sheet adhered to the polymer membrane from the substrate surface to obtain the cultured multi-layered cell sheet adhered to the polymer membrane.

8. A cultured multi-layered cell sheet adhered to a polymer membrane for grafting, wherein the cell sheet is produced by the process according to claim 7.

9. A therapeutic method in which the cultured multi-layered cell sheet produced according to the method of claim 7 is grafted to a burn and/or a wound that are gouged deep into a skin tissue.

10. A process for producing a cultured multi-layered cell sheet adhered to a polymer membrane, wherein said cell sheet is used for grafting and comprises fibroblasts or angioendothelial cells and mucous membrane cells, comprising
    (1) providing a cellular sheet or multi-layered cell sheet adhered to a temperature-responsive polymer which has been coated on a cell culture support, wherein the temperature-responsive polymer has a lower critical solution temperature in water of 0-80° C. and is poly(N-isopropylacrylamide), wherein the cellular sheet is provided in culture solution, and wherein the cellular sheet comprises fibroblasts or angioendothelial cells;
    (2) adhering the cultured multi-layered cell sheet adhered to the polymer membrane obtained by the process according to claim 1 to cellular sheet or multi-layered cell sheet provided in step (1);
    (3) adjusting the temperature of the culture solution to below the lower critical solution temperature, whereby the substrate surface is made hydrophilic and adhesion of the cell sheet to the substrate is weakened; and
    (4) peeling the cultured multi-layered cell sheet adhered to the polymer membrane from the substrate surface without treatment with a proteolytic enzyme to obtain the cultured multi-layered cell sheet adhered to the polymer membrane.

11. A cultured multi-layered cell sheet adhered to a polymer membrane for grafting, wherein the cell sheet is produced by the process according to claim 10.

12. A therapeutic method in which the cultured multi-layered cell sheet produced according to the method of claim 10 is grafted to a burn and/or a wound that are gouged deep into a skin tissue.

13. The process according to any one of claims 1, 4, 7 or 10 wherein the polymer membrane is hydrophilized polyvinylidene difluoride.

* * * * *